United States Patent
Zhang et al.

(10) Patent No.: US 11,129,847 B2
(45) Date of Patent: Sep. 28, 2021

(54) ANTIBACTERIAL WOUND DRESSING, METHOD FOR PREPARING THE SAME, AND USE THEREOF

(71) Applicant: Huizhou Foryou Medical Devices Co., Ltd., Huizhou (CN)

(72) Inventors: Junfeng Zhang, Huizhou (CN); Jinwen Mo, Huizhou (CN); Jie Dong, Huizhou (CN)

(73) Assignee: HUIZHOU FORYOU MEDICAL DEVICES CO., LTD., Huizhou (CN)

( * ) Notice: Subject to any disclaimer, the term of this patent is extended or adjusted under 35 U.S.C. 154(b) by 191 days.

(21) Appl. No.: 16/435,559

(22) Filed: Jun. 10, 2019

(65) Prior Publication Data

US 2019/0290676 A1 Sep. 26, 2019

Related U.S. Application Data (63) Continuation-in-part of application No. PCT/CN2017/085429, filed on May 23, 2017.

(51) Int. Cl.
| | | |
|---|---|---|
| *A61K 31/717* | (2006.01) | |
| *A61P 17/02* | (2006.01) | |
| *A61K 9/00* | (2006.01) | |
| *A61L 15/46* | (2006.01) | |
| *A61L 15/28* | (2006.01) | |

(52) U.S. Cl.
CPC .......... *A61K 31/717* (2013.01); *A61K 9/0014* (2013.01); *A61L 15/28* (2013.01); *A61L 15/46* (2013.01); *A61P 17/02* (2018.01)

(58) Field of Classification Search
CPC ....... C08B 11/12; C08B 11/15; A61K 31/717; A61K 9/0014; A61P 17/02; A61L 2300/404; A61L 2300/206
See application file for complete search history.

(56) References Cited

U.S. PATENT DOCUMENTS

| | | |
|---|---|---|
| 6,075,177 A | 6/2000 | Bahia et al. |
| 6,605,751 B1 | 8/2003 | Gibbins et al. |
| 8,828,424 B2 | 9/2014 | Bray |
| 2003/0203991 A1 | 10/2003 | Schottman et al. |
| 2005/0101900 A1 | 5/2005 | Qin et al. |
| 2010/0215723 A1 | 8/2010 | Yao |
| 2013/0150765 A1 | 6/2013 | Moghe et al. |

FOREIGN PATENT DOCUMENTS

| | | |
|---|---|---|
| CN | 102462860 A | 5/2012 |
| CN | 102675651 B | 6/2014 |
| CN | 104805734 A | 7/2015 |
| CN | 103920180 B | 1/2016 |
| CN | 102580136 B | 3/2016 |
| GB | 1328088 A | 8/1973 |
| JP | 1992146218 A | 5/1992 |
| WO | WO1991011206 A1 | 8/1991 |
| WO | WO1992022285 A1 | 12/1992 |
| WO | WO2009080239 A2 | 7/2009 |
| WO | WO2014020133 A2 | 2/2014 |

OTHER PUBLICATIONS

Zhi et al., ACS Appl. Mater. Interfaces, 2017, 9, p. 10383-10397. (Year: 2017).*
European search report,EP17910932, dated May 19, 2020 (11 pages).
Database WPI—Week 201616 Thomson Scientific, London, GB; AN 2015-56748N-XP002798825.

\* cited by examiner

*Primary Examiner* — Jonathan S Lau (57) ABSTRACT

An antibacterial wound dressing, a method for preparing the antibacterial wound dressing, and a use of the antibacterial wound dressing are provided. The antibacterial wound dressing is obtained by amidating carboxymethyl cellulose with a guanidine compound. The carboxymethyl cellulose has a substitution degree of 0.1-0.6, and the guanidine compound has a grafting degree of 0.2%-10.0%.

19 Claims, 1 Drawing Sheet

ANTIBACTERIAL WOUND DRESSING, METHOD FOR PREPARING THE SAME, AND USE THEREOF

CROSS REFERENCE TO RELATED APPLICATIONS

The present application is a continuation-application of International (PCT) Patent Application No. PCT/CN2017/085429 filed May 23, 2017, the entire contents of which are hereby incorporated by reference in their entireties.

TECHNICAL FIELD

The present disclosure relates to the field of wound care or wound healing medicine, and in particular, to an antibacterial wound dressing, a method for preparing the antibacterial wound dressing, and a use of the antibacterial wound dressing.

BACKGROUND

Natural cellulose is the most widely distributed and most abundant polysaccharide in nature, and has a very rich source. At present, the cellulose is improved mainly in etherification and esterification. Carboxymethylation reaction is one technique for the etherification. Carboxymethylation of cellulose can generate carboxymethyl cellulose (CMC). An aqueous solution of the carboxymethyl cellulose has the functions of thickening, film formation, adhesion, moisture retention, colloid protection, emulsification, suspension, and the like. The carboxymethyl cellulose is widely used in industries of petroleum, food, medicine, textile, papermaking, and the like, and is one of the most important cellulose ethers. The carboxymethyl cellulose has the ability to absorb a great deal of water and to form a gel on the surface of the carboxymethyl cellulose. This property of the carboxymethyl cellulose material has been found to be advantageous in the preparation of wound dressings that are both absorbent and gel-forming, and the use of the carboxymethyl cellulose for wound dressing is described in WO-A-94/16746.

At present, sterilizing agents for killing bacteria or harmful microorganisms mainly include natural antibacterial agents (such as chitosan and its derivatives, and the like), inorganic antibacterial agents (such as silver-based antibacterial agents, and the like), and organic antibacterial agents (such as quaternary ammonium salts, guanidine salts, phenols, ethers, pyrroles, and the like). Silver is a useful antibacterial agent with a broad-spectrum activity together with a compatibility with mammalian tissues. Silver-salt solution can be used to sterilize by disrupting cell walls of bacteria and denaturing bacterial enzymes. There have been many proposals to incorporate silver into wound dressings to obtain the advantages of the antibacterial properties of silver in the wound dressings. Many patent documents, such as GB-A-1,328,088, WO-A-91/11206, WO-A-92/22285, JP-A-4146218, WO-A-02/36866, WO-A-01/24839, U.S. Pat. No. 8,828,424B2, and CN102580136B, have disclosed the technical solution of incorporating silver into calcium sodium alginate or CMC to prepare antibacterial dressings. However, many experts believe that silver ions will be precipitated from the dressing and further enter human bodies, thereby causing coagulation of proteins, which in turns results in a damage to skin surfaces. In this way, it may have harmful influence on human health and there is a potential safety hazard. Chitosan, which belongs to the natural antibacterial agents, is also an effective antibacterial agent. China Patent Nos. CN102675651B and CN103920180B disclose an antibacterial hydrogel formed by grafting biguanide onto chitosan. No precipitations will be precipitated from the antibacterial hydrogel prepared by the above method, and the antibacterial agent is safe. However, the preparation processes of the hydrogel are complicated, and the hydrogel is capable of absorbing only a small amount of liquid. Besides, the chitosan is a product obtained from an animal source, such that the chitosan is immunogenic, and thus there is still a potential safety hazard.

Guanidine salt is a commonly used organic antibacterial agent. China Patent No. CN 102,462,860 discloses an antibacterial fiber-based wound dressing and a preparation method of the wound dressing. The wound dressing is a fabric made of fibers which is sprayed with polyhexamethylene biguanide solution, or a fabric sprayed with the polyhexamethylene biguanide solution. The wound dressing can be continuously used for 7 days. However, the polyhexamethylene biguanide component is only adsorbed on the fabric and is easily precipitated from the fabric. After the polyhexamethylene biguanide component is precipitated from the fabric, the antibacterial properties of the dressing are decreased.

SUMMARY

Based on this, in order to overcome the defects in the related art, the present disclosure provides an antibacterial wound dressing having an excellent antibacterial effect, and the antibacterial rate of the antibacterial wound dressing is not less than 99% in seven days. The antibacterial wound dressing is capable of absorbing a large amount of liquid, and has a good liquid holding capacity after the antibacterial wound dressing absorbs liquid, and a good moisture-retaining capacity. The antibacterial wound dressing also has good biocompatibility without sensitization, irritation, and immunogenicity.

In another aspect, the present disclosure further provides a method for preparing the antibacterial wound dressing.

The technical solution of the present disclosure is described as follow.

Figure 1:
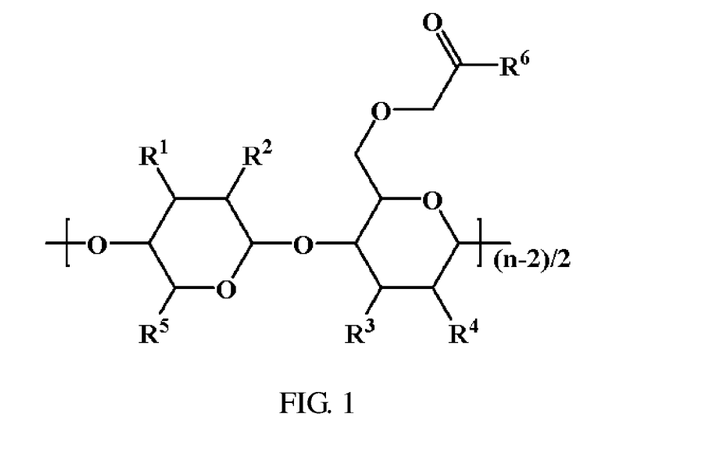
FIG. 1 illustrates a structural formula of an antibacterial wound dressing.

An antibacterial wound dressing has a structural formula I:

(I)

$R^1$, $R^2$, $R^3$ and $R^4$ each is —OH or —OCH$_2$COONa; $R^5$ is —CH$_2$OH or —CH$_2$OCH$_2$COONa. $R^6$ is H or -continued $R^7$ is $Cl^-$, $H_2PO_4^-$, $CH_3CH_2COO^-$, or $CH_2OH(CHOH)_4COO^-$, n=200-800, m=10-100.

In the present disclosure, the antibacterial wound dressing uses carboxymethyl cellulose as the main chain and uses a guanidine compound as the side chain. The carboxymethyl cellulose has the ability to absorb a great deal of water and to form a gel on the surface of the carboxymethyl cellulose. This property of the carboxymethyl cellulose has been found to be advantageous in the preparation of wound dressings that are both absorbent and gel-forming. The guanidine compound is an environmental-friendly polymeric disinfectant and an efficient broad-spectrum antibacterial agent. The guanidine compound has excellent properties including such as a fast acting speed, being stable, being soluble in water, and the like. Besides, the guanidine compound can be used at room temperature, and perform long-term antibacterial activities. The guanidine compound is non-toxic, odorless, non-corrosive, free of side effects, and safe to use. The antibacterial wound dressing of the present disclosure has excellent antibacterial effect, and the antibacterial rate is not less than 99% in seven days. The antibacterial wound dressing has a large liquid absorption amount, a good liquid holding capacity after the antibacterial wound dressing absorbs liquid, and a good moisture-retaining capacity. In addition, the antibacterial wound dressing of the present disclosure has a good biocompatibility without sensitization, irritation, and immunogenicity.

In one embodiment, n=200-500. When the antibacterial wound dressing has a polymerization degree of 200-500, the antibacterial wound dressing may perform a good liquid absorption ability.

In one embodiment, the antibacterial wound dressing may be obtained by the carboxymethyl cellulose and a guanidine compound, and the connection between the carboxymethyl cellulose and the guanidine compound is an amide bond. A substitution degree of the carboxymethyl cellulose may range from 0.1 to 0.6, and a grafting degree of the guanidine compound can range from 0.2% to 10.0%.

In one embodiment, the substitution degree of the carboxymethyl cellulose may range from 0.2 to 0.5.

In one embodiment, the guanidine compound may be polyhexamethylene guanidine and a derivative thereof, or polyhexamethylene biguanide and a derivative thereof.

In one embodiment, the guanidine compound may be polyhexamethylene guanidine hydrochloride, polyhexamethylene biguanide hydrochloride, polyhexamethylene guanidine phosphate, polyhexamethylene guanidine propionate, or polyhexamethylene guanidine gluconate.

In one embodiment, the grafting degree of the guanidine compound may range from 0.5% to 9.0%.

In one embodiment, the grafting degree of the guanidine compound may range from 0.5% to 5.0%.

In one embodiment, the carboxymethyl cellulose may include one raw material selected from the group consisting of a lyocell fiber, a cotton fiber, a bamboo fiber and a viscose fiber.

The method for preparing the antibacterial wound dressing may comprise the following blocks. S1, cellulose is alkalized with sodium hydroxide by means of a solvent method wherein water and ethanol are used as the reaction media, such that an alkali cellulose is obtained, and the alkali cellulose is etherified with chloroacetic acid to prepare carboxymethyl cellulose having a substitution degree of 0.1-0.6.

S2, a carboxymethyl cellulose-organic solvent suspension having a mass/volume ratio of 0.5%-40% is prepared.

S3, an activating agent or an acid regulating agent, and a condensing agent is added into the carboxymethyl cellulose-organic solvent suspension, a guanidine compound is further added, and a reaction is performed at 0° C.-50° C. for 0.5 hour-48 hours.

S4, unreacted small molecular substances are removed, and a drying treatment is performed to obtain the antibacterial wound dressing.

In one embodiment, an organic solvent of the carboxymethyl cellulose-organic solvent suspension is at least one solvent selected from a group consisting of toluene, acetone, butanone, tetrahydrofuran, chloroform, dimethylacetamide, dimethylformamide, dimethyl sulfoxide, dichloromethane, chloroform, acetonitrile, and pyridine.

In one embodiment, the activating agent is N-hydroxysuccinimide or 1-hydroxybenzotriazole.

In one embodiment, the amount of the activating agent to be used is 0.1%-10% by mass of the carboxymethyl cellulose.

In one embodiment, the condensing agent may be a water-soluble carbodiimide compound. More specifically, the water-soluble carbodiimide compound may be 1-(3-dimethylaminopropyl)-3-ethylcarbodiimide hydrochloride, N,N'-dicyclohexylcarbodiimide, or N,N'-diisopropylcarbodiimide.

In one embodiment, the amount of the condensing agent to be used may be 0.15%-15% by mass of the carboxymethyl cellulose.

In one embodiment, the acid regulating agent may be a mineral acid, such as hydrochloric acid or sulfuric acid.

In one embodiment, the acid regulating agent may be configured to control a PH of the reaction system to be 4-6.

In one embodiment, S1 may include the following blocks.

1) Raw lyocell having a polymerization degree of 300-1200 may be mixed with and react with sodium hydroxide aqueous solution and ethanol at a temperature of 15° C.-40° C. for 30 min-90 min. A mass ratio of the raw lyocell, the sodium hydroxide, the water, and the ethanol may be 1:(0.3-3.0):(3.0-6.0):(6.0-9.0).

2) Chloroacetic acid may be further added, and a reaction may be controlled to be performed at a reaction temperature of 30° C.-54° C. for 1 hour-3 hours, then performed at a temperature of 55° C.-75° C. for 1 hour-3 hours. A mass ratio of the raw lyocell and the chloroacetic acid may be 1:(0.2-1).

3) Glacial acetic acid may be added for neutralization. The neutralization reaction may be performed at a temperature of 20° C.-45° C. for 30 min-90 min. A mass/volume ratio of the raw lyocell to the glacial acetic acid may be 1:0.25. Washing may be performed by ethanol and water and then a drying treatment may be further performed, such that the carboxymethyl cellulose may be obtained.

In one embodiment, S2 may include the following block. The carboxymethyl cellulose may be mixed with an organic solvent, such that the carboxymethyl cellulose-organic solvent suspension having a mass/volume ratio of 0.5%-40% may be prepared.

In one embodiment, the carboxymethyl cellulose-organic solvent suspension has the mass/volume ratio of 10%-30%.

In one embodiment, S3 may include the following block. A condensing agent, an activating agent, and a guanidine compound may be added to the carboxymethyl cellulose-organic solvent suspension, and an amidation reaction may be performed at a temperature of 20° C.-50° C. for 30 min-240 min. A mass ratio of the condensing agent, the activating agent, the guanidine compound, and the carboxymethyl cellulose is set in such a way that, the mass ratio of carboxymethyl cellulose:condensing agent:activating agent:guanidine compound is 1:(0.015-0.15):(0.01-0.1):(0.02-6).

In one embodiment, the reaction in S3 is performed at a temperature of 35° C. for 120 min.

In one embodiment, S4 may include the following block. A mixed solution of ethanol and water may be added for washing, wherein the ethanol may be at the concentration of 83%-86%. The washing may be performed at a temperature of 35° C.-45° C. for 20 min to remove unreacted small molecular substances. After that, a drying treatment may be further performed at 50° C. to obtain the antibacterial wound dressing.

The present disclosure further discloses a use of the antibacterial wound dressing in acute or chronic wound care.

In one embodiment, the antimicrobial wound dressing is a woven or nonwoven fabric.

The present disclosure may have the following beneficial effects. In the present disclosure, an efficient antibacterial wound dressing may be prepared by grafting the guanidine compound onto the carboxymethyl cellulose by an amidation reaction, and the efficient antibacterial wound dressing combines both the properties of the carboxymethyl cellulose (including such as fast liquid absorption, good moisture retention, good gel protection, and the like) with antibacterial properties of the guanidine compound. The present disclosure has excellent antibacterial effects by controlling the grafting degree of the guanidine compound, and the antibacterial rate is not less than 99% in seven days. Besides, the antibacterial wound dressing has a large liquid absorption amount, a good liquid holding capacity after the antibacterial wound dressing absorbs liquid, and a good moisture-retaining capacity. The antibacterial wound dressing also has a good biocompatibility without sensitization, irritation, and immunogenicity.

DETAILED DESCRIPTION

The present disclosure will now be described in detail with reference to the drawings and embodiments. The examples described below are merely illustrative of the embodiments of the present disclosure, and the description of the examples is specific and detailed. However, it cannot be constructed as a limitation to the protection scope of the present disclosure. All technical solutions obtained from equivalent substitutions or transformations should fall within the scope of protection of the present disclosure.

In one aspect, an antibacterial wound dressing is provided. The antibacterial wound dressing may have a structural formula I:

In this case, $R^1$, $R^2$, $R^3$ and $R^4$ each is —OH or —OCH$_2$COONa; $R^5$ is —CH$_2$OH or —CH$_2$OCH$_2$COONa. $R^6$ is $R^7$ is Cl$^-$, H$_2$PO$_4^-$, CH$_3$CH$_2$COO$^-$, or CH$_2$OH(CHOH)$_4$COO$^-$, n=200-800, m=10-100.

In the present disclosure, the antibacterial wound dressing uses carboxymethyl cellulose as the main chain, and uses a guanidine compound as the side chain. The carboxymethyl cellulose has the ability to absorb a great deal of water and to form a gel on the surface of the carboxymethyl cellulose. This property of the carboxymethyl cellulose has been found to be advantageous in the preparation of wound dressings that are both absorbent and gel-forming. The guanidine compound is an environmental-friendly polymeric disinfectant, and is an efficient broad-spectrum antibacterial agent. The guanidine compound has excellent properties including such as a fast acting speed, being stable, being soluble in water, and the like. Besides, the guanidine compound can be used at room temperature, and perform long-term antibacterial activities. The guanidine compound is non-toxic, odorless, non-corrosive, free of side effects, and safe to use. The antibacterial wound dressing of the present disclosure has an excellent antibacterial effect, and the antibacterial rate is not less than 99% in seven days. The antibacterial wound dressing has a large liquid absorption amount, a good liquid holding capacity after the antibacterial wound dressing absorbs liquid, and a good moisture-retaining capacity. In addition, the antibacterial wound dressing of the present disclosure has a good biocompatibility without sensitization, irritation, and immunogenicity.

In some embodiments, n=200-500. When the antibacterial wound dressing has a polymerization degree of 200-500, the antibacterial wound dressing may perform a good liquid absorption ability.

In some embodiments, the antibacterial wound dressing may be obtained by the carboxymethyl cellulose amidated with a guanidine compound. A substitution degree of the carboxymethyl cellulose may range from 0.1 to 0.6, and a grafting degree of the guanidine compound may range from 0.2% to 10.0%.

In some embodiments, the substitution degree of the carboxymethyl cellulose may range from 0.2 to 0.5.

In some embodiments, the guanidine compound may be polyhexamethylene guanidine and a derivative thereof, or polyhexamethylene biguanide and a derivative thereof.

In some embodiments, the guanidine compound may be polyhexamethylene guanidine hydrochloride, polyhexamethylene biguanide hydrochloride, polyhexamethylene guanidine phosphate, polyhexamethylene guanidine propionate, or polyhexamethylene guanidine gluconate.

In some embodiments, the grafting degree of the guanidine compound may range from 0.5% to 9.0%.

In some embodiments, the grafting degree of the guanidine compound may range from 0.5% to 5.0%.

In some embodiments, the carboxymethyl cellulose may include one raw material selected from the group consisting of a lyocell fiber, a cotton fiber, a bamboo fiber and a viscose fiber.

In another aspect, a method for preparing the antibacterial wound dressing may be further provided. The method may include the following blocks.

S1, cellulose is alkalized with sodium hydroxide by means of a solvent method wherein water and ethanol are used as the reaction media, such that an alkali cellulose is obtained, and the alkali cellulose is etherified with chloroacetic acid to prepare carboxymethyl cellulose having a substitution degree of 0.1-0.6.

S2, a carboxymethyl cellulose-organic solvent suspension having a mass/volume ratio of 0.5%-40% is prepared.

S3, an activating agent or an acid regulating agent and a condensing agent is added into the carboxymethyl cellulose-organic solvent suspension, a guanidine compound is further added, and a reaction is performed at 0° C.-50° C. for 0.5 hour-48 hours.

S4, unreacted small molecular substances are removed, and a drying treatment is performed to obtain the antibacterial wound dressing.

In some embodiments, an organic solvent of the carboxymethyl cellulose-organic solvent suspension is at least one solvent selected from a group consisting of toluene, acetone, butanone, tetrahydrofuran, chloroform, dimethylacetamide, dimethylformamide, dimethyl sulfoxide, dichloromethane, chloroform, acetonitrile, and pyridine.

In some embodiments, the activating agent is N-hydroxysuccinimide or 1-hydroxybenzotriazole.

In some embodiments, the amount of the activating agent to be used is 0.1%~10% by mass of the carboxymethyl cellulose.

In some embodiments, the condensing agent may be a water-soluble carbodiimide compound. More specifically, the water-soluble carbodiimide compound may be 1-(3-dimethylaminopropyl)-3-ethylcarbodiimide hydrochloride, N,N'-dicyclohexylcarbodiimide, or N,N'-diisopropylcarbodiimide.

In some embodiments, the amount of the condensing agent to be used may be 0.15%-15% by mass of the carboxymethyl cellulose.

In some embodiments, the acid regulating agent may be a mineral acid, such as hydrochloric acid or sulfuric acid.

In some embodiments, the acid regulating agent may be configured to control a PH of the reaction system to be 4-6.

In some embodiments, S1 may include the following blocks.

1) Raw lyocell having a polymerization degree of 300-1200 may be mixed with and react with sodium hydroxide aqueous solution and ethanol at a temperature of 15° C.-40° C. for 30 min-90 min. A mass ratio of the raw lyocell, the sodium hydroxide, the water, and the ethanol may be 1:(0.3-3.0):(3.0-6.0):(6.0-9.0).

2) Chloroacetic acid may be further added, and a reaction may be controlled to be performed at a reaction temperature of 30° C.-54° C. for 1 hour-3 hours, then performed at a temperature of 55° C.-75° C. for 1 hour-3 hours. A mass ratio of the raw lyocell and the chloroacetic acid may be 1:(0.2-1).

3) Glacial acetic acid may be added for neutralization. The neutralization reaction may be performed at a temperature of 20° C.-45° C. for 30 min-90 min. A mass/volume ratio of the raw lyocell to the glacial acetic acid may be 1:0.25. Washing may be performed by ethanol and water and then a drying treatment may be further performed, such that the carboxymethyl cellulose may be obtained.

In some embodiments, S2 may include the following block. The carboxymethyl cellulose may be mixed with an organic solvent, such that the carboxymethyl cellulose-organic solvent suspension having a mass/volume ratio of 0.5%-40% may be prepared.

In some embodiments, the carboxymethyl cellulose-organic solvent suspension has the mass/volume ratio of 10%-30%.

In some embodiments, S3 may include the following block. A condensing agent, an activating agent, and a guanidine compound may be added to the carboxymethyl cellulose-organic solvent suspension, and an amidation reaction may be performed at a temperature of 20° C.-50° C. for 30 min-240 min. A mass ratio of the condensing agent, the activating agent, the guanidine compound, and the carboxymethyl cellulose is set in such a way that, the mass ratio of carboxymethyl cellulose:condensing agent:activating agent:guanidine compound is 1:(0.015-0.15):(0.01-0.1):(0.02-6).

In some embodiments, the reaction in S3 is performed at a temperature of 35° C. for 120 min.

In some embodiments, S4 may include the following block. A mixed solution of ethanol and water may be added for washing, wherein the ethanol may be at the concentration of 83%-86%. The washing may be performed at a temperature of 35° C.-45° C. for 20 min to remove unreacted small molecular substances. After that, a drying treatment may be further performed at 50° C. to obtain the antibacterial wound dressing.

In a further aspect, a use of the antibacterial wound dressing in acute or chronic wound care may be further provided in the present disclosure.

In one embodiment, the antimicrobial wound dressing is a woven or nonwoven fabric.

Example 1

Materials used in the following examples are all commercially available products, unless otherwise stated.

In the following examples, a substitution degree of carboxymethyl cellulose is measured by using Method 5.5 in Food additive—Sodium carboxymethyl cellulose in standard GB 1904-2005.

In the following examples, a grafting degree of a guanidine compound in an antimicrobial wound dressing is measure by using the method disclosed in Appendix A in the hygienic standard for biguanides disinfectants in standard GB 26367-2010.

Example 1

An antibacterial wound dressing may be prepared by the following blocks.

S1, raw lyocell having a polymerization degree of 600-1000 may be mixed with and react with sodium hydroxide aqueous solution and ethanol at a temperature of 30° C.-40° C. for 60 min. The mass of the raw lyocell in the mixed solution may be 1.0 Kg, the mass of the sodium hydroxide in the mixed solution may be 2.0 Kg, the mass of the water in the mixed solution may be 5.0 Kg, and the mass of the ethanol the mixed solution may be 7.0 Kg, respectively. 0.3 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be performed by using ethanol and water and then a drying treatment may be further performed, such that the carboxymethyl cellulose may be obtained. The measurement results indicate that the carboxymethyl cellulose has a substitution degree of 0.3 and a polymerization degree of 421.

S2, the carboxymethyl cellulose may be mixed with an organic solvent (in this case, acetone is used as the organic solvent) and water, and a carboxymethyl cellulose-organic solvent suspension having a mass/volume ratio of 20% may be prepared.

S3, a condensing agent EDS (1-(3-dimethylaminopropyl)-3-ethylcarbodiimide hydrochlorid), an activating agent NHS (N-hydroxysuccinimide), and a guanidine compound of polyhexamethylene biguanide hydrochloride (PHMB, m=50-80) may be further added into the carboxymethyl cellulose-organic solvent suspension, and an amidation reaction may be performed at a temperature of 30° C. for 120 min. In this case, the mass ratio of the condensing agent, the activating agent, the guanidine compound to the carboxymethyl cellulose may be set as follow. A mass ratio of (carboxymethyl cellulose):(condensing agent):(activating agent):(guanidine compound) may be 1:0.04:0.025:0.25.

S4, a mixed solution of ethanol and water may be added for washing, wherein the ethanol may be at the concentration of 83%-86%. In this case, the washing may be performed at a temperature of 35° C.-45° C. for 20 min to remove unreacted small molecular substances. After that, a drying treatment may be further performed at 50° C. to obtain an antibacterial wound dressing. The measurement results indicate that a grafting degree of the PHMB in the antibacterial wound dressing is 2.0%.

Figure 2:
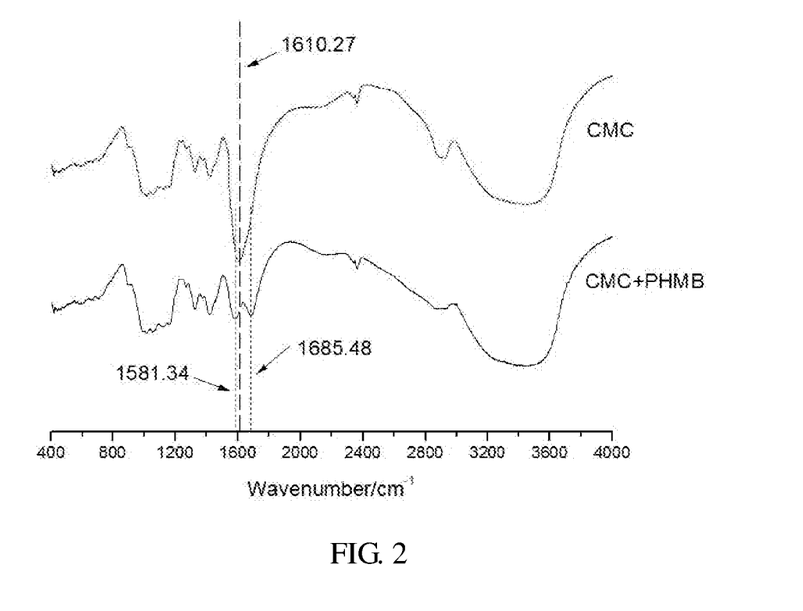
FIG. 2 illustrates an infrared spectrum of carboxymethyl cellulose and the antimicrobial wound dressing.

An infrared spectrum of the raw lyocell and the antibacterial wound dressing prepared by the raw lyocell used in this example may be shown in FIG. 2. It can be seen from FIG. 2 that, the antibacterial wound dressing prepared in this example has a characteristic peak indicating amide bond at a position near 1581 cm$^{-1}$ and a position near 1685 cm$^{-1}$, which indicates that the PHMB has been successfully grafted onto the carboxymethyl cellulose, and thus the target product may be obtained.

Example 2

An antibacterial wound dressing may be prepared by the following blocks.

S1, raw lyocell having a polymerization degree of 600-1000 may be mixed with and react with sodium hydroxide aqueous solution and ethanol at a temperature of 30° C.-40° C. for 60 min. The mass of the raw lyocell, the sodium hydroxide, the water, and the ethanol in the mixed solution may be 1.0 Kg, 2.0 Kg, 5.0 Kg, and 7.0 Kg, respectively. 0.3 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be then performed by using ethanol and water and a drying treatment may be further performed after that, such that the carboxymethyl cellulose may be obtained. The measurement results indicate that the carboxymethyl cellulose has a substitution degree of 0.3 and a polymerization degree of 421.

S2, the carboxymethyl cellulose may be mixed with an organic solvent (in this case, acetone is used as the organic solvent) and water, and a carboxymethyl cellulose-organic solvent suspension having a mass/volume ratio of 20% may be prepared.

S3, a condensing agent EDS, an activating agent NHS, and a guanidine compound of polyhexamethylene guanidine phosphate may be further added into the carboxymethyl cellulose-organic solvent suspension, and an amidation reaction may be performed at a temperature of 30° C. for 60 min. In this case, the mass ratio of the condensing agent, the activating agent, the guanidine compound to the carboxymethyl cellulose may be set as follow. A mass ratio of (carboxymethyl cellulose):(condensing agent):(activating agent):(guanidine compound) may be 1:0.108:0.066:1.5.

S4, a mixed solution of ethanol and water may be added for washing, wherein the ethanol may be at the concentration of 83%-86%. In this case, the washing may be performed at a temperature of 37° C.-43° C. for 20 min to remove unreacted small molecular substances. After that, a drying treatment may be further performed at 50° C. to obtain an antibacterial wound dressing. The measurement results indicate that a grafting degree of the polyhexamethyl guanidine phosphate in the antibacterial wound dressing is 6.5%.

Example 3

An antibacterial wound dressing may be prepared by the following blocks.

S1, raw lyocell having a polymerization degree of 600-1000 may be mixed with and react with sodium hydroxide aqueous solution and ethanol at a temperature of 30° C.-40° C. for 60 min. The mass of the raw lyocell, the sodium hydroxide, the water, and the ethanol in the mixed solution may be 1.0 Kg, 2.0 Kg, 5.0 Kg, and 7.0 Kg, respectively. 0.3 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be then performed by using ethanol and water and a drying treatment may be further performed after that, such that the carboxymethyl cellulose may be obtained. The measurement results indicate that the carboxymethyl cellulose has a substitution degree of 0.3 and a polymerization degree of 421.

S2, the carboxymethyl cellulose may be mixed with an organic solvent (in this case, acetone is used as the organic solvent) and water, and a carboxymethyl cellulose-organic solvent suspension having a mass/volume ratio of 20% may be prepared.

S3, a condensing agent EDS, an activating agent NHS, and a guanidine compound of polyhexamethylene guanidine propionate may be further added into the carboxymethyl cellulose-organic solvent suspension, and an amidation reaction may be performed at a temperature of 30° C. for 60 min. In this case, the mass ratio of the condensing agent, the activating agent, the guanidine compound to the carboxymethyl cellulose may be set as follow. A mass ratio of (carboxymethyl cellulose):(condensing agent):(activating agent):(guanidine compound) may be 1:0.072:0.044:0.6.

S4, a mixed solution of ethanol and water may be added for washing, wherein the ethanol may be at the concentration of 83%-86%. In this case, the washing may be performed at a temperature of 37° C.-43° C. for 20 min to remove unreacted small molecular substances. After that, a drying treatment may be further performed at 50° C. to obtain an antibacterial wound dressing. The measurement results indicate that a grafting degree of the polyhexamethylene guanidine propionate in the antibacterial wound dressing is 3.6%.

Example 4

An antibacterial wound dressing may be prepared by the following blocks.

S1, raw lyocell having a polymerization degree of 600-1000 may be mixed with and react with sodium hydroxide aqueous solution and ethanol at a temperature of 30° C.-40° C. for 60 min. The mass of the raw lyocell, the sodium hydroxide, the water, and the ethanol in the mixed solution may be 1.0 Kg, 2.0 Kg, 5.0 Kg, and 7.0 Kg, respectively. 0.3 Kg of chloroacetic acid may be further added, and a reaction may be controlled to be performed at a reaction temperature of 40° C.~-50° C. for 60 min, then performed at a temperature of 55° C.-65° C. for 60 min. 0.25 L of glacial acetic acid may be added for neutralization at a temperature of 25° C.-30° C. for 60 min. Washing may be then performed by using ethanol and water and a drying treatment may be further performed after that, such that the carboxymethyl cellulose may be obtained. The measurement results indicate that the carboxymethyl cellulose has a substitution degree of 0.3 and a polymerization degree of 421.

S2, the carboxymethyl cellulose may be mixed with an organic solvent (in this case, acetone is used as the organic solvent) and water, and a carboxymethyl cellulose-organic solvent suspension having a mass/volume ratio of 20% may be prepared.

S3, a condensing agent EDS, an activating agent NHS, a guanidine compound of polyhexamethylene guanidine gluconate may be further added into the carboxymethyl cellulose-organic solvent suspension, and an amidation reaction may be performed at a temperature of 30° C. for 60 min. In this case, the mass ratio of the condensing agent, the activating agent, the guanidine compound to the carboxymethyl cellulose may be set as follow. A mass ratio of (carboxymethyl cellulose):(condensing agent):(activating agent):(guanidine compound) may be 1:0.15:0.1:3.2.

S4, a mixed solution of ethanol and water may be added for washing, wherein the ethanol may be at the concentration of 83%-86%. In this case, the washing may be performed at a temperature of 37° C.-43° C. for 20 min to remove unreacted small molecular substances. After that, a drying treatment may be further performed at 50° C. to obtain an antibacterial wound dressing. The measurement results indicate that a grafting degree of the polyhexamethylene guanidine gluconate in the antibacterial wound dressing is 8.7%.

Example 5

Raw lyocell having a polymerization degree of 600-1000 may be mixed with and react with sodium hydroxide aqueous solution and ethanol at a temperature of 30° C.-40° C. for 60 min. The mass of the raw lyocell, the sodium hydroxide, the water, and the ethanol in the mixed solution may be 1.0 Kg, 2.0 Kg, 5.0 Kg, and 7.0 Kg, respectively. 0.2 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be performed by using ethanol and water and then a drying treatment may be further performed, such that the carboxymethyl cellulose may be obtained. The measurement results indicate that the carboxymethyl cellulose has a substitution degree of 0.18 and a polymerization degree of 537.

The carboxymethyl cellulose may be further grafted with the polyhexamethylene biguanide hydrochloride (PHMB) by the method described in the blocks S2, S3 and S4 of Example 1 to obtain the antibacterial wound dressing, and the grafting degree of the PHMB in the antibacterial wound dressing is indicated to be 0.21%.

Example 6

Raw lyocell having a polymerization degree of 600-1000 may be mixed with and react with sodium hydroxide aqueous solution and ethanol at a temperature of 30° C.-40° C. for 60 min. The mass of the raw lyocell, the sodium hydroxide, the water, and the ethanol in the mixed solution may be 1.0 Kg, 2.0 Kg, 5.0 Kg, and 7.0 Kg, respectively. 0.55 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be performed by using ethanol and water and then a drying treatment may be further performed, such that the carboxymethyl cellulose may be obtained. The measurement results indicate that the carboxymethyl cellulose has a substitution degree of 0.48 and a polymerization degree of 368.

The carboxymethyl cellulose may be further grafted with the polyhexamethylene biguanide hydrochloride (PHMB) by the method described in the blocks S2, S3 and S4 of Example 1 to obtain the antibacterial wound dressing, and the grafting degree of the PHMB in the antibacterial wound dressing is indicated to be 3.8%.

Example 7

An antibacterial wound dressing may be prepared by the following blocks.

S1, raw lyocell having a polymerization degree of 600-1000 may be mixed with and react with sodium hydroxide aqueous solution and ethanol at a temperature of 30° C.-40° C. for 60 min. The mass of the raw lyocell, the sodium hydroxide, the water, and the ethanol in the mixed solution may be 1.0 Kg, 2.0 Kg, 5.0 Kg, and 7.0 Kg, respectively. 0.7 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be performed by using ethanol and water and then a drying treatment may be further performed, such that the carboxymethyl cellulose may be obtained. The measurement results indicate that the carboxymethyl cellulose has a substitution degree of 0.6 and a polymerization degree of 320.

The carboxymethyl cellulose may be further grafted with the polyhexamethylene biguanide hydrochloride (PHMB) by the method described in the blocks S2, S3 and S4 of Example 1 to obtain the antibacterial wound dressing, and the grafting degree of the PHMB in the antibacterial wound dressing is indicated to be 7.2%.

Example 8

A raw viscose fiber having a polymerization degree of 300-600 may be provided, and treated as the method described in Example 1, to obtain the carboxymethyl cellulose. The measurement results indicate that the carboxymethyl cellulose has a substitution degree of 0.33 and a polymerization degree of 227. After that, an antibacterial wound dressing may be prepared according to the method described in Example 1. The measurement results indicate that the grafting degree of the PHMB in the antibacterial wound dressing is 2.5%.

Example 9

A raw cotton fiber having a polymerization degree of 1000-1200 may be provided, and treated as the method described in Example 1, to obtain the carboxymethyl cellulose. The measurement results indicate that the carboxymethyl cellulose has a substitution degree of 0.25 and a polymerization degree of 694. After that, an antibacterial wound dressing may be prepared according to the method described in Example 1. The measurement results indicate that the grafting degree of the PHMB in the antibacterial wound dressing is 1.1%.

Comparative Example 1

An antibacterial wound dressing may be prepared by the following blocks.

Raw cotton fiber having polymerization degree of 1500-18000 may be mixed with and react with sodium hydroxide aqueous solution and ethanol at a temperature of 30° C.-40° C. for 60 min. The mass of the raw cotton fiber, sodium hydroxide, water, and ethanol in the mixed solution may be 1.0 Kg, 2.0 Kg, 5.0 Kg, and 7.0 Kg, respectively. 0.1 Kg of chloroacetic acid may be further added, and a reaction may be controlled to be performed at a reaction temperature of 40° C.-50° C. for 60 min, then performed at a temperature of 55° C.-65° C. for 60 min. 0.25 L of glacial acetic acid may be added for neutralization at a temperature of 25° C.-30° C. for 60 min. Washing may be performed by using ethanol and water and then a drying treatment may be further performed, such that the carboxymethyl cellulose may be obtained. The measurement results indicate that the carboxymethyl cellulose has a substitution degree of 0.08 and a polymerization degree of 877.

The carboxymethyl cellulose may be further grafted with the polyhexamethylene biguanide hydrochloride (PHMB) by the method described in the blocks S2, S3 and S4 of Example 1 to obtain the antibacterial wound dressing, and the grafting degree of the PHMB in the antibacterial wound dressing is indicated to be 0.12%.

The antibacterial wound dressings respectively prepared in Examples 1 to 9 and Comparative Example 1 may be measured for liquid absorption amount, biocompatibility, and antibacterial property. The measurement results may be shown in Table 1. The measurement standards or methods may be as follows.

(1) Liquid Absorption Amount: 0.3 g of sample which has been dried by blowing gas at 80° C. for 2 hours may be weighed and further placed into a watch glass. Test solution A (the test solution A is a solution composed of sodium chloride and calcium chloride; the solution contains 142 mmol of sodium ions and 2.5 mmol of calcium ions; the ion content in the solution corresponds to that in the human serum or the wound fluid; 8.298 g of sodium chloride and 0.368 g of calcium chloride dihydrate are dissolved and diluted to 1 L by deionized water in a volumetric flask) may be slowly added by dropwise into the sample, until the sample may be saturated by the liquid. A weight of the sample after absorbing the test solution A may be weighed, and the liquid absorption amount may be calculated by using the formula (W-0.3)/0.3*100%.

Antibacterial property: the Antibacterial property may be measured by using the shake flask method described in part 3 in the GBT 20944.3-2008 Textiles-Evaluation for antibacterial activity. Test strains include *Enterococcus faecalis* (ATCC 51575) and *Pseudomonas aeruginosa* (ATCC 9027).

Liquid holding capacity: a sample may be cut into a size of 50 mm*50 mm, and weighed. The weight may be recorded as W1. The sample may be further placed into the watch glass, and a certain amount of the test solution A (the test solution A is a solution composed of sodium chloride and calcium chloride; the solution contains 142 mmol of sodium ions and 2.5 mmol of calcium ions; the ion content in the solution corresponds to that in the human serum or the wound fluid; 8.298 g of sodium chloride and 0.368 g of calcium chloride dihydrate are dissolved and diluted to 1 L by deionized water in a volumetric flask) may be added, until the sample is saturated with the absorbed liquid. The sample having the saturated liquid absorption amount may be further placed on a plane, and a pressure of 40 mmHg (about 1.36 kg) may be applied to a surface of the sample (50 mm*50 mm) for 5 min, the liquid exuded from the sample may be further sucked away. The sample may be then taken out, and weighed again; the weight of the sample may be recorded as W2 at this time. Enough filter papers may be placed on the sample. The filter papers may be further removed after 30 min. At this time, the sample may be weighed again and the weight of the sample may be recorded as W3. The liquid holding capacity may be calculated by the following formula: (W3−W1)/(W2−W1)*100%.

TABLE 1

Performance Test Result of Antibacterial Wound Dressing of Examples and Comparative Example

| Test items | Liquid Absorption Amount/% | Antibacterial property/% | Liquid holding capacity/% |
|---|---|---|---|
| Example 1 | 2660 | 99.99 | 83.57 |
| Example 2 | 2484 | 99.99 | 79.40 |
| Example 3 | 2533 | 99.99 | 80.25 |
| Example 4 | 2400 | 99.99 | 78.66 |
| Example 5 | 2187 | 99.99 | 71.32 |
| Example 6 | 1933 | 99.99 | 77.68 |
| Example 7 | 1795 | 99.99 | 74.72 |
| Example 8 | 935 | 99.99 | 81.68 |
| Example 9 | 3292 | 99.99 | 82.21 |
| Comparative Example 1 | 1680 | 70.23 | 52.44 |

To verify the biocompatibility of the antibacterial wound dressings, tests for cytotoxicity (ISO 10993-5: 2009), acute toxicity (ISO 10993-11: 2006), skin sensitization (ISO 10993-10: 2010) and skin irritation (ISO 10993-10:2010) may be performed to the antibacterial wound dressings. The test results indicate that the prepared antibacterial wound dressings are biocompatible.

The technical features of the above-mentioned embodiments may be combined in any combination. For a brief and concise description, all possible combinations of the technical features in the above embodiments are not described. Those skilled in the art may make many variations and modifications without departing from the spirit and scope of the present disclosure. All these belong to the scope of the present disclosure.

What is claimed is:

1. An antibacterial wound dressing, having a structural formula I:

wherein $R^1$, $R^2$, $R^3$ and $R^4$ each is —OH or —OCH$_2$COONa; $R^5$ is —CH$_2$OH or —CH$_2$OCH$_2$COONa; $R^6$ is wherein $R^7$ is Cl$^-$, H$_2$PO$_4^-$, CH$_3$CH$_2$COO$^-$, or CH$_2$OH(CHOH)$_4$COO$^-$, n=200-800, m=10-100; the antibacterial wound dressing is obtained by carboxymethyl cellulose and a guanidine compound, and the connection between the carboxymethyl cellulose and the guanidine compound is an amide bond; a substitution degree of the carboxymethyl cellulose is in a range of 0.1 to 0.5.

2. The antibacterial wound dressing of claim 1, wherein n=200-500.

3. The antibacterial wound dressing of claim 1, wherein the substitution degree of the carboxymethyl cellulose is in a range of 0.18 to 0.3, a grafting degree of the guanidine compound is ranged from 0.2% to 10.0%.

4. The antibacterial wound dressing of claim 3, wherein the substitution degree of the carboxymethyl cellulose is ranged from 0.2 to 0.5.

5. The antibacterial wound dressing of claim 3, wherein the guanidine compound is polyhexamethylene guanidine and a derivative thereof, or polyhexamethylene biguanide and a derivative thereof.

6. The antibacterial wound dressing of claim 5, wherein the guanidine compound is polyhexamethylene guanidine hydrochloride, polyhexamethylene biguanide hydrochloride, polyhexamethylene guanidine phosphate, polyhexamethylene guanidine propionate, or polyhexamethylene guanidine gluconate.

7. The antibacterial wound dressing of claim 6, wherein the grafting degree of the guanidine compound is ranged from 0.5% to 9.0%.

8. The antibacterial wound dressing of claim 7, wherein the grafting degree of the guanidine compound is ranged from 0.5% to 5.0%.

9. The antibacterial wound dressing of claim 3, wherein the carboxymethyl cellulose comprises one raw material selected from the group consisting of a lyocell fiber, a cotton fiber, a bamboo fiber and a viscose fiber.

10. A method for preparing an antibacterial wound dressing, comprising:

S1, alkalizing cellulose with sodium hydroxide by means of a solvent method by using water and ethanol as reaction media, such that an alkali cellulose is obtained, and etherifying the alkali cellulose with chloroacetic acid to prepare carboxymethyl cellulose having a substitution degree of 0.1-0.5;

S2, preparing a carboxymethyl cellulose-organic solvent suspension having a mass/volume ratio of 0.5%-40%;

S3, adding an activating agent or an acid regulating agent and a condensing agent into the carboxymethyl cellulose-organic solvent suspension, further adding a guanidine compound, and performing a reaction at 0° C.-50° C. for 0.5 hour-48 hours; and S4, removing unreacted small molecular substances, and performing a drying treatment to obtain the antibacterial wound dressing;

wherein the antibacterial wound dressing has a structural formula I:

$R^1$, $R^2$, $R^3$ and $R^4$ each is —OH or —OCH$_2$COONa; $R^5$ is —CH$_2$OH or —CH$_2$OCH$_2$COONa; $R^6$ is -continued $R^7$ is $Cl^-$, $H_2PO_4^-$, $CH_3CH_2COO^-$, or $CH_2OH(CHOH)_4COO^-$, n=200-800, m=10-100; the antibacterial wound dressing is obtained by the carboxymethyl cellulose and the guanidine compound, and the connection between the carboxymethyl cellulose and the guanidine compound is an amide bond.

11. The method of claim 10, wherein an organic solvent of the carboxymethyl cellulose-organic solvent suspension is at least one solvent selected from a group consisting of toluene, acetone, butanone, tetrahydrofuran, chloroform, dimethylacetamide, dimethylformamide, dimethyl sulfoxide, dichloromethane, chloroform, acetonitrile, and pyridine.

12. The method of claim 10, wherein the activating agent is N-hydroxysuccinimide or 1-hydroxybenzotriazole.

13. The method of claim 10, wherein the condensing agent is a water-soluble carbodiimide compound.

14. The method of claim 10, wherein S3 comprises: adding the condensing agent, the activating agent, and the guanidine compound to the carboxymethyl cellulose-organic solvent suspension, and performing an amidation reaction at a temperature of 20° C.-50° C. for 30 min-240 min; wherein a mass ratio of the condensing agent, the activating agent, the guanidine compound, and the carboxymethyl cellulose is set in such a way that, the mass ratio of carboxymethyl cellulose:condensing agent:activating agent:guanidine compound is 1:(0.015-0.15):(0.01-0.1):(0.02-6).

15. The method of claim 10, wherein S1 comprises: mixing and reacting raw lyocell having a polymerization degree of 300-1200 with sodium hydroxide aqueous solution and ethanol at a temperature of 15° C.-40° C. for 30 min-90 min; wherein a mass ratio of the raw lyocell, the sodium hydroxide, the water, and the ethanol is 1:(0.3-3.0):(3.0-6.0):(6.0-9.0);

adding chloroacetic acid, performing a reaction at a reaction temperature of 30° C.-54° C. for 1 hour-3 hours, then heating up to perform the reaction at a temperature of 55° C.-75° C. for 1 hour-3 hours; wherein a mass ratio of the raw lyocell and the chloroacetic acid is 1:(0.2-1);

adding glacial acetic acid to perform a neutralization reaction at a temperature of 20° C.-45° C. for 30 min-90 min; wherein a mass/volume ratio of the raw lyocell to the glacial acetic acid is 1:0.25; and performing a washing by using ethanol and water and then performing a drying treatment, such that the carboxymethyl cellulose may be obtained.

16. The method of claim 10, wherein S2 comprises: mixing the carboxymethyl cellulose mixed with an organic solvent, such that the carboxymethyl cellulose-organic solvent suspension having a mass/volume ratio of 0.5%-40% is prepared.

17. The method of claim 10, wherein S4 comprises: adding a mixed solution of ethanol and water for washing; wherein the ethanol is at the concentration of 83%-86%; the washing is performed at a temperature of 35° C.-45° C. for 20 min to remove unreacted small molecular substances; and performing a drying treatment at 50° C. to obtain the antibacterial wound dressing.

18. The method of claim 10, wherein the activating agent is N-hydroxysuccinimide or 1-hydroxybenzotriazole, and the condensing agent is a water-soluble carbodiimide compound.

19. The method of claim 10, wherein the amount of the activating agent to be used is 0.1%-10% by mass of the carboxymethyl cellulose, and the amount of the condensing agent to be used is 0.15%-15% by mass of the carboxymethyl cellulose.

* * * * *